United States Patent
Elsner

(12)
(10) Patent No.: US 6,281,241 B1
(45) Date of Patent: Aug. 28, 2001

(54) USE OF MELATONIN FOR THE TREATMENT OF ANDROGENETIC ALOPECIA

(75) Inventor: Peter Elsner, Meilen (CH)

(73) Assignee: ASAT AG Applied Science and Technology, Zug (CH)

( * ) Notice: Subject to any disclaimer, the term of this patent is extended or adjusted under 35 U.S.C. 154(b) by 0 days.

(21) Appl. No.: 09/506,442

(22) Filed: Feb. 18, 2000

(30) Foreign Application Priority Data

Nov. 30, 1999 (DE) .............................. 199 57 710

(51) Int. Cl.⁷ ...................... A61K 31/405; A61K 31/195
(52) U.S. Cl. ............................. 514/415; 514/561
(58) Field of Search .................... 514/415, 561, 514/182; 424/401

(56) References Cited

U.S. PATENT DOCUMENTS 4,746,674   5/1988   Pierpaoli et al. .................... 514/415

FOREIGN PATENT DOCUMENTS 2 101 660   *   7/1997   (ES) .
WO 98/05298 *   2/1998   (WO) .
WO 99/32072 *   7/1999   (WO) .

OTHER PUBLICATIONS

Ludwig, "Classification of the types of androgenetic alopecia (common baldness) occurring in the female sex", British Journal of Dermatology (1977) 97, 247.

Rougeot et al., 1986, Ann. Zootech, 35(4), 363–71.

* cited by examiner

*Primary Examiner*—Zohreh Fay
*Assistant Examiner*—Brian-Yong Kwon
(74) *Attorney, Agent, or Firm*—Arent Fox Plotkin Kintner Kahn, PLLC.

(57) ABSTRACT

The invention relates to the use of melatonin and melatonin-containing preparations for the treatment of androgenetic alopecia of the female type.

7 Claims, No Drawings

USE OF MELATONIN FOR THE TREATMENT OF ANDROGENETIC ALOPECIA

The invention relates to the use of melatonin and melatonin-containing preparations for the treatment of androgenetic alopecia of the female type.

Melatonin (N-acetyl-5-methoxytryptamine) is a hormone with a broad spectrum of action [1,2], produced and secreted from the pineal gland under the influence of β-adrenergic receptors having a circadian rhythm. Although the mechanisms of the action of melatonin are still not comprehensively clarified in detail, melatonin appears to control the adaptation of the organism to environmental stimuli, in particular light and temperature. The toxicity of melatonin is not detectable, even on oral administration of several grams per day [3]. In the case of topical application in a nanocolloid preparation, and of alcoholic solutions, no local or systemic side effects were seen in over 60 subjects. Animal experimental studies indicate that the systemic administration of melatonin improves the thickness and structure of coat hair [4,5].

The influence of the duration of daylight exposure to the seasonal change of coat has been described for the sheep [6], the Kashmir goat and some other species of goat [7], red deer [8] and mink [9]. The mitotic activity of the secondary follicles and the hair growth resulting therefrom increases from the beginning of summer until the winter, to stop in the spring. After a resting stage, in which the hairs of the primary and secondary follicles fall out, a new growth cycle begins with induction of a new anagenic phase.

This cycle of hair growth and of molting is disturbed if the pineal gland is removed [5]. Welch [10] was able to show that by administration of melatonin in cashmere goats the initialization of the growth activity of the secondary follicles in the spring can be accelerated. In New Zealand, goats were treated with melatonin over a period of 14 days in order to initiate the spring growth, and compared with untreated goats. The histological examination of biopsies of the skin which were taken during the 14 days showed, in the goats which had been treated with melatonin, an induction of hair growth by changeover of the hair follicle from the telogenic phase to the proanagenic phase, while the hair follicles of the untreated goats remained in the telogenic phase [11].

In in-vitro investigations of hair follicles of the cashmere goat in the hair organ culture model, it was likewise possible to detect the influence of melatonin on the hair growth of the follicle. In the 24 hour interval, the administration of melatonin in concentrations from 150 mg/ml led to a greater growth of the hair shafts than the lower dose and the control. Over the total period of 120 hours, the differences in the longitudinal growth were significant (p =0.05). The best growth rates and maximal total growth after 120 hours were recorded with the administration of the melatonin concentration of 300 ng/l [12].

U.S. Pat. No. 4,476,674 discloses the use of melatonin for the treatment of various disorders in humans which are accompanied by hair loss, namely the treatment of toxic alopecia, e.g. alopecia induced by treatment with medicaments, and the treatment of alopecia of the male type. A reference to the use of melatonin for treatment in the case of androgenetic alopecia of the female type is not found.

Androgenetic alopecia of the female type differs significantly from toxic alopecia. Significant differences also exist with respect to androgenetic alopecia of the male type, namely with respect to the clinical intensity, the mechanism of action and the treatability.

1. Differences in the Clinical Intensity

Although androgenetic alopecia occurs in both sexes, the clinical intensity is typically different.

The hair loss pattern of the male type (male pattern alopecia) has already been described by Hamilton in 1942 and modified by Eblin and Rook in 1972. In this, marked receding of the hairline is seen in stage 1, which is accompanied from stage 2 with increasing thinning of the occipital hair and then with increasing confluence of both areas in stage 4 results in the appearance of a largely bald scalp with a residual fringe of hair in the occipital region [13, 14].

The hair loss pattern of the female type (female pattern alopecia) differs markedly from the male type, as in this form no receding of the hairline occurs and complete baldness of the scalp never results. This form was divided into three stages by Ludwig, with especially the centroparietal (crown of the head) region diffusely thinning out as the stages progress. Even in the case of advanced alopecia in women, there is usually still a thin fringe of hair of 1 to 2 cm between the forehead and thinned crown region [15].

2. Differences in the Mechanism of Action

The term "androgenetic alopecia" is understood as meaning forms of hair loss which occur under the influence of androgens in the presence of a genetic disposition. They are associated with an acceleration of the hair cycle, which leads to the proliferation of telogenic hairs and increasing occurrence of thin miniature hairs.

In men, the high androgen levels, together with the given constitutional sensitivity of the hair roots to androgens, regularly lead to male alopecia.

In women, who have 10 times lower androgen levels than men, the absolute amount of androgen is less responsible for the development of hair loss than the increased end organ sensitivity to androgens. In over 90% of women, this mechanism leads to female pattern alopecia, while in the other cases male pattern alopecia can also occur. In this case, increased androgen levels are often found [16]. Likewise, a rare female pattern alopecia can occur in men, which in this case too has no similarity to male pattern alopecia and also does not change into this.

3. Differences in Treatability

Differences are also seen in the therapeutic mechanisms of action.

The studies extensively carried out in recent years on alopecia in men showed a very good response of a 5-alpha-reductase inhibitor (finasteride), which inhibits the conversion of testosterone to dihydrotestosterone. It was possible to achieve stopping of the hair loss in 80% of the cases and a slight to marked improvement in the hair density in 66% of the cases [17]. Thus the pathological mechanism of the male hair loss type still seems to be limited rather by the amount of androgens reacted than by the sensitivity of the roots.

Up to now, unpublished data on experiments with finasteride in postmenopausal women did not show any superior efficacy compared with placebo. This gives the decisive reference to the increased sensitivity of the hair roots to the small amounts of androgens present in women.

Moreover, the use of finasteride in women of childbearing age is contraindicated, as reduced levels of dihydrotestosterone, the active metabolite of testosterone, in a male fetus can lead to malformations of the external genitals.

In a scientific investigation leading to the present patent application, it has now been found that melatonin is a suitable active compound for the treatment of androgenetic alopecia of the female type. Significantly better results from the use of melatonin in androgenetic alopecia in women compared with those of diffuse alopecia in women were found with respect to the telogenic rates. The use of melatonin in androgenetic alopecia in women is thus to be delimited as a specific medicinal indication from androgenetic alopecia in men and diffuse alopecia in women and implies a novel principle of action. It can be presumed that melatonin, in the androgen-mediated mechanism in women, develops modulating properties which are not effective in men on account of the high androgen concentration.

For the treatment of androgenetic alopecia of the female type, a melatonin preparation is preferably applied topically. Application can take place here in the form of sprays, solutions, lotions, creams, ointments, shampoos, conditioners or other suitable forms. In addition to the active compound, the preparations can contain suitable vehicles, diluents or excipients and, if appropriate, further pharmacologically active compounds such as, for example, vitamins, e.g. vitamins C, E and/or H. Examples of suitable vehicles are water, aqueous buffers, alcohol or lipophilic substances. If appropriate, excipients can be employed which improve the absorption and penetration of the active compound (see U.S. Pat. No. 4,746,674).

The melatonin preparation can have, for example, an active compound concentration of 0.001 to 1% (wt/wt). Preferably, the active compound concentration lies in ranges from 0.01 to 0.5% (wt/wt). The active compound dose applied daily depends on the severity of the disorder and the type of application. Thus active compound doses of 0.001 to 10 mg, in particular of 0.1 to 5 mg, per day and patient have proven suitable.

By means of the administration of melatonin, a reduction in the telogenic rate is surprisingly achieved. The telogenic rate in the range of below 20% characterizes a physiological hair loss, i.e. hair falling out is replaced by newly growing hair. A telogenic rate of 20% is to be considered here as an upper limit of a normal range, the majority of the findings varying in a range from 5% to 15%. If the telogenic rate exceeds 20%, a net loss of hair occurs, in which hair falling out can no longer be completely replaced by newly growing hair. An increasing thinning of the hair results from this. By administration of melatonin, it was possible to achieve a reduction in the telogenic rate of a value increased above the norm in the normal range, i.e. below 20%.

Furthermore, in patients having androgenetic alopecia of the female type an enlargement of the hair diameter and/or an increase in the power of resistance of the hair, in particular in the case of frontal hair, but also in the case of occipital hair, is found due to the administration of melatonin.

Even in the case of diffuse alopecia of the female type, an action of the melatonin preparation was found. This action was admittedly not so pronounced as in androgenetic alopecia, nevertheless a significant enlargement of the hair diameter and an increase in the extensibility were observed, in particular in the case of occipital hair.

The invention thus also relates to the use of melatonin for the enlargement of the hair diameter and/or increase in the extensibility in the case of diffuse alopecia, in particular in the case of occipital hair and female patients.

While the melatonin plasma levels admittedly increase under administration of melatonin compared with a placebo treatment, they do not exceed the physiological night level of 250 pg/ml. In the subjects treated with melatonin, no increased occurrence of tiredness was seen compared with the placebo group, such that the safety profile of the melatonin application used could be classified as good.

The invention will furthermore be illustrated in the context of the following examples.

EXAMPLES

1. Methodology

Study Design

The trial was carried out as a randomized, placebo-controlled double-blind study on 40 female patients having diffuse or androgenetic, non-ulotic alopecia, who, after clarification, declared themselves willing to participate in the investigation.

Trial procedure

A daily evening topical treatment of the scalp with 8 strokes of 0.128 ml of 0.1% melatonin spray, corresponding to 1.024 ml daily, or administration of melatonin-free alcoholic solution (placebo) was carried out. The treatment period was 6 months. The hair growth and the mechanical hair quality were determined by means of trichograms and also measurements of the hair shaft diameter and the tensile strength. Checks on the plasma melatonin level were carried out.

Subjects 40 women of 20 to 70 years of age with healthy skin and good general health and having androgenetic or diffuse alopecia were tested. Care was taken that none of the women were pregnant or lactating, there was no dermatological local therapy on the scalp and no ulotic alopecia was present. Furthermore, no hair-cosmetic measures were carried out during the study.

Washing Phase

Before the beginning of the study, each patient had to carry out a one-week washing phase using a neutral shampoo (Every-Day-Shampoo®, Sebapharma, Boppard, Germany).

Test Substance 0.1% melatonin in alcoholic solution (30% ethanol, 70% water, v/v) in light-protected aluminum bottles having a standardized spray head and placebo in alcoholic solution (30% ethanol, 70% water; v/v) in light-protected aluminum bottles having a standardized spray head were in each case used in a number-coded randomized distribution.

The test products were handed over at the beginning of the study as a packet having 6 spray bottles for the treatment period of 6 months. One bottle in each case contained 33 ml corresponding to a month's supply.

Target Parameters

Trichogram

For the investigation of the anagenic and telogenic rates, trichograms were prepared. In this procedure, 5 days in each case after the last hair wash 30 to 50 hairs were obtained frontally approximately 2 cm from the forehead/hair boundary and laterally from the sagittal line in a standardized manner by epilation using a special hairgrip. A 2nd epilation was taken occipitally 2 cm laterally of the protuberantia occipitalis. The trichograms were carried out before the beginning of the study, and after 3 and 6 month's treatment. The hair roots obtained were mounted on slides, analogously counted by means of a light microscope at 20-times magnification and the percentage ratios of the anagenic, telogenic and dystrophic hairs were calculated.

Hair Shaft Measurements

From the hair samples obtained for the trichogram, frontally and occipitally at least 10 hairs in each case were used for the hair shaft measurements. These samples were investigated before the beginning of the preparation application and after 3 and 6 months's treatment.

Diameter

For the measurement of the diameter and of the mechanical properties of the hair, 5 hairs from the frontal and occipital taking region of the trichogram were in each case used.

Breaking Force

For the measurement of the force which had to be used in order to break the hair, the hairs were first stretched, by means of a computer-controlled measuring and control unit at a constant force (Newton), to breaking point.

Breaking Distance

In a manner analagous to the determination of the breaking force, it was possible to determine the stretching distance up to the breaking point by means of the measuring unit. The stretching distance was measured in mm.

Melatonin Plasma Levels

Melatonin plasma levels were determined by means of a commercially obtainable radioimmunoassay (RIA, DPC Biermann GmbH, Bad Neuheim, Germany).

Patient Questionnaire

Undesirable pharmaceutical side effects were determined by means of a patient questionnaire. At the end of the study, an additional termination questionnaire was filled in by the patients, in which they could express their views on the success of the therapy, on the chronological occurrence of side effects and on the administration form of the preparation.

Data and Statistics

All the individual data from the trichogram investigations, the hair shaft measurements and the melatonin measurements were recorded in Microsoft Excel and mean values and standard deviations were calculated. The statistical analysis of the measured values at the various points in time in the two treatment groups was carried out by the SPSS statistics program.

2. Results

Study Population

A total of 40 female patients were admitted into the study, 12 women having androgenetic alopecia and 28 women diffuse alopecia. The clinical severity of the androgenetic alopecia ranged from the stage Ludwig I to III, that of diffuse alopecia from slightly to moderately pronounced. In none of the patients was there an internal condition or another local condition of the scalp apart from alopecia.

Trichograms

The trichograms were carried out according to plan at the beginning of the 6-month investigation period, after the 3rd month and the 6th month (final measurement). For the overall analysis, the anagenic and telogenic rates of both condition groups were combined.

Frontal Trichograms

In the placebo group, the analysis of the frontal trichograms showed a relatively constant anagenic rate of 82.2% before therapy, 82% after two months and 82.2% after six months. The telogenic rate correspondingly behaved similarly, a slight decrease from 17.2% to 16.8% being recorded at the end of the investigation period. The rate of dystrophic hairs varied in the normal range of below 4%. In the drug group, a slight increase in the anagenic rate from 80.4% to 82.6% was observed. The telogenic rate decreased from 18.9% to 16.8% and 15.9%. A proportion of 0.6% to 2.2% of the dystrophic hairs had a normal rate. The differences in the anagenic and telogenic rates after 3 and 6 months's treatment compared with the starting values were not significant either in the placebo group or in the drug group.

Occipital Trichograms

On inspection of the occipital trichograms, the placebo group initially showed a decrease in the anagenic rate from 80.4% to 79.5% up to month 3 and a subsequent increase to 84.1% by month 6.

The telogenic rate increased up to month 3 from 16.8% to 19.2% and by month 6 decreased to 14.0%.

The changes in the placebo group were not significant either for the anagenic rates or for the telogenic rates.

The anagenic rates of the drug group, however, showed a marked continuous increase from 76.3% to 78.8% (month 3) and 85% to month 6. The difference in the anagenic rate between the starting result and month 6 was significant (p $\leq 0.021$).

Still more pronounced changes were seen both after 3 months' and after 6 months' treatment in the telogenic rate of the drug group. They fell from 23.03% to 18.1% from month 1 to month 3. Up to month 6, a decrease to 12.5% was achieved. Thus, by means of 6 month's treatment with drug, a reduction in the telogenic rate to approximately half was achieved. At p <0.048, the difference from month 3 to month 6 was significant and over the entire observation period of 6 months it was highly significant (p <0.005).

Analysis of the Diagnostic Groups (alopecia androgenetica vs. alopecia diffusa)

On account of the significant differences in the occipital trichograms of the drug group, a division was carried out as a function of the various diagnoses.

Androgenetic alopecia

Under placebo (n =6), the 12 patients having androgenetic alopecia showed constant anagenic and telogenic rates of 78.22% to 82.11% or 17.6% and 17.2%. The anagenic rates in patients of the drug group (n=6) increased from 73.6% to 87.8%. Even more marked differences in the telogenic rates were found with a decrease from 26.5% to 18.3% (month 3) and 10.8% (month 6). In this case, the decrease from the starting result to month 6 was significant with p <0.035.

Diffuse alopecia

In the 28 patients with diffuse alopecia, under placebo administration (n=14) a slight increase in the anagenic rate from 81.39% to 84.89% and a decrease in the telogenic rate from 16.4% to 12.66% was seen.

In patients of the drug group (n=14), an increase in the anagenic rate from 77.4% to 83.7% was recorded. The telogenic rate decreased from 21.6% to 13.2%. These differences, however, were not statistically significant.

Measurement of the Physical Hair Parameters

Measurements of the hair diameter of hair taken frontally showed an enlargement of the diameter in 67% of the patients of the drug group having the diagnosis androgenetic alopecia. The power of resistance of hair of patients under melatonin treatment increased from 0.56 N to 0.61 N after 6 month's treatment. In the frontal hair, no further improvements were otherwise seen compared with the placebo group with respect to the physical hair parameters.

In investigations on hair taken occipitally, an enlargement of the hair diameter was seen in 55% of patients treated with melatonin and an increase in the stretching force in 70% of the patients. The improvements due to melatonin were observed particularly in the group having diffuse alopecia (86%).

Melatonin Plasma Levels

The melatonin plasma levels in the placebo group lay at values between 2 and 10 pg/ml with individual peak values of up to 80 pg/ml. In some cases considerable intra- and inter-individual differences were found.

In the drug group, the melatonin plasma levels at the measurement time 1 before application lay in the range from 2 to 10 pg/ml and increased at the following measurement times to values of on average 30 to 50 pg/ml. Individual peak values lay at 180 pg/ml. In this group too, considerable intra- and inter-individual differences in the measured values were seen. Despite the application of melatonin, the physiological average melatonin peak in the night of 250 pg/ml was not exceeded in this group.

Furthermore, an accumulation in the melatonin serum level did not occur. The melatonin plasma levels remained constant between 30 and 50 pg/ml over the investigation period of 6 months.

Patient Questionnaire

Success of the Therapy

The hair loss was classified in the placebo group by a total of 56% of the patients as improved, by 36% as stopped and by 13% as worsened.

In the drug group, 69% of the patients stated that the hair loss had improved, in 23% the hair loss had stopped and only in 8% had the hair loss worsened.

Side Effects

During the entire study period, no objective changes occurred in the region of the application site, in particular there was no allergic contact eczema or irritative eczema of the scalp. Epilation for carrying out the trichograms and the mechanical measurements of the hair was well tolerated by all participants and bleeding or an ongoing hair loss at the taking site did not occur in any single case. As a sign of a slight irritation due to the alcoholic vehicle of the preparation, itching occurred in some subjects. This was recorded in the case of 6 subjects at the start of the study and only in the case of 4 in the later course of the study. With respect to other side effects such as reddening, flaking and greasiness, which were subjectively expressed by the patients and objectivized by the physician, and of purely subjectively perceived symptoms such as burning of the scalp and the feeling of tightness, no differences occurred between the two test groups.

Tiredness as a side effect of the therapy was also seen both in 4 patients who had been treated with placebo and in 4 patients who had been treated with melatonin. However, in the case of 3 patients of the melatonin group tiredness was indicated in the course of the study, while in the placebo group this side effect only occurred initially.

Acceptance of the Preparation

The preparation size was classified as good by the majority of the users (85%). The spray form was indicated as suitable by 91% and the application was generally classified as practical by almost all patients (97%).

3. Discussion

In the present study, a significant efficacy of the topical 0.1% strength melatonin preparation at a dose of 1 ml daily was shown on the telogenic rate in the occipital region. While the quality of the hair with respect to its diameter and its stretching properties was not significantly influenced by the melatonin preparation in contrast to the placebo, clear differences between verum and placebo were seen in the trichogram results. In the overall analysis of the findings of all patients, a significant increase in anagenic hair ($p \leq 0.021$) and a decrease in telogenic hair ($p \leq 0.005$) was seen, especially in the occipital trichograms at the end of the 6-month treatment period. On examination of the telogenic hair, a significant difference was seen even from month 3 to month 6 ($p \leq 0.048$). The rate of the dystrophic hair was always in the normal range, such that no harmful actions of the preparation on the physiological hair root were observed. As the determination of the hair root status by the trichogram shows a percentage ratio of anagenic, telogenic and dystrophic hairs, it inevitably results that changes in one hair type repeatedly also cause changes in the other type. In spite of this, the determination of the telogenic rate as a parameter of the hair loss is to be classified as particularly important, since the light-microscopic assessment of the telogenic hair as pigment-free, club-shaped hair without a root sheath is clearly to be carried out. The anagenic hair class, on the other hand, subsumes various hair types such as, for example, anagenic hairs with and without root sheaths, broken-off hairs and dysplastic anagenic hair. Difficulties in discrimination sometimes result here with the dystrophic hair, which is not to be included in the anagenic hair. For this reason, all trichograms which had an inconclusive result with respect to the dystrophic hair and anagenic hair were subjected to a plausibility check and complete counting again.

In the region of below 20%, the telogenic rate characterizes physiological hair loss, i.e. the hair falling out is replaced by newly growing hair. The rate of 20% is to be considered as an upper limit of a normal range, in which the majority of the results vary in a range from 5% to 15%. If the telogenic rate exceeds 20%, a net loss of the hair occurs, in which the hair falling out can no longer be completely replaced by newly growing hair. An increasing thinning of the hair results from this. In the present study, it was possible to detect the significant reduction in the telogenic rate in the occipital region, where a decrease from 23% to 12.5% occurred. The telogenic rate, which was increased slightly above the norm at the beginning of the study, thus lay completely in the normal range at the end of the 6-month treatment period. In the analysis separated according to diagnostic groups, it was seen that the group having androgenetic alopecia profited most from the use of the preparation, in particular in the occipital scalp region. At a starting rate of 26.5% telogenic hair, the melatonin preparation achieved a reduction to 18.3% after 3 months use and to 10.8% after 6 months. The differences were significant from month 1 to month 6 at $p \leq 0.035$.

The positive effects on the telogenic rates of the frontal hair samples were admittedly likewise stronger than those of the placebo, due to the use of the melatonin preparation, but showed no significant differences. This is to be explained by the fact that especially in androgenetic alopecia, the area of the crown of the head where the frontal trichograms are taken is most severely affected by hair loss, as the androgen sensitivity of the hair roots is typically most pronounced here.

In the case of diffuse alopecia, the action of the melatonin preparation is admittedly present, but not pronounced to such an extent as in androgenetic alopecia. Diffuse alopecia represents a symptom-orientated diagnosis which is not specified in greater detail, in which various causes such as nutritive factors, noxae and perfusion disorders of the scalp disturb the physiological equilibrium of the hair growth. Here, melatonin can likewise be effective as a promoter of anagen induction, but only under the condition that other harmful factors do not predominate.

The melatonin plasma levels admittedly increased under melatonin administration, compared with the placebo treatment, but not over the physiological night level of 250 pg/ml. The effect to be expected of increased melatonin plasma levels on the vigilance of the subjects has been recorded by the patient questionnaires. Compared with the placebo group., no increased occurrence of tiredness is seen, such that the safety profile of the melatonin preparation used is to be classified as good in the case of topical application to the scalp.

References

1. Arendt J. The pineal. In: Touitou Y, Haus E. eds. Biological Rhythm in Clinical and laboratory medicine, 1992
2. Cardinali D P (1981) Melatonin. A mammalian pineal hormone. Endocr Rev. 2:327–46
3. Gonzalez R. Sanches A, Ferguson J et al. (1991) Melatonin therapy of advanced human malignant melanoma. Melanoma research 1:237–243
4. Lesnikov V A, Pierpaoli W (1994) Pineal cross-transplantation (old-to-young and vice versa) as evidence for an endogenous "aging clock". Ann N Y Acad Sci 31:56–60
5. Allain, D, Ravault J P, Panaretto B A, Rougeot J (1986) Effects of pinealectomy on photoperiodic control of hair follicle activity in the Limousine ram: possible relationship with plasma prolactin levels. J Pin Res 3:25–32
6. Lincoln G A, Klansdorf H, Anderson N (1980) Photoperiodic control of thyroid function and wool and horn growth in rams and the effect of cranial sympathectomy. Endocrinology 107:1543–1548
7. Ryder M L, Cashmere, Mohair and Other Luxury Animal Fibres for the Breeder and Spinner. Itchen, Southampton, 1987, pp 1–23
8. Webster J R, Barrel G K (1985) Advancement of reproductive activity, seasonal reduction in prolactin secretion and seasonal pelage changes in pubertal red deer hinds (Cervus elaphus) subjected to artificially shortened daily photoperiod or daily melatonin treatments. J Reprod Fertil 73:255–260
9. Bissonette T H, Wilson E (1939) Shortening daylight periods between May 15 and September 12 and the pelt cycle in mink. Science 89:418–419
10. Welch R A S, Grunsey M, Betteridge K, Mitchell R J (1990) Goat fibre response to melatonin given in spring in two consecutive years. Proc. NZ Soc Anim Prod 50:335–338
11. Nixon A J, Choj V J, Parry A L, Pearson A J (1993) Fiber growth initiation in hair follicles of goats treated with melatonin, J Exp Zool 267:47–56
12. Ibraheem M, Galbraith H, Scaife J, Ewen S (1994) Growth of secondary hair follicles of the Cashmere goat in vitro and their response to prolactin and melatonin. J Anat 185:135–142
13. Ebling F J, Root A: Hair. In: Rook A, Wilkinson D S, Ebling F J (eds.): Textbook of Dermatology, Blackwell, Oxford, 1972, pp 1355–1425
14. Hamilton J B, (1942) Male hormone stimulation is prerequisite and an incitant in common baldness. Am J Anat 71:451–480
15. Ludwig E (1977) Classification of the types of androgenetic alopecia (common baldness) occurring in the female sex. Brit J Derm 97 237–254
16. Orfanos C E, Haar and Haarkrankheiten Hair and hair diseases, Gustav Fischer Verlag, Stuttgart-New York, 1991, pp. 573–584
17. Kauffmann K D, Olsen E A, Whiting D et al. (1998), Finasteride in the treatment of men with androgenetic alopecia. J Am Acad Dermatol, (1998) 39:578–589

What is claimed is:

1. A method for the treatment of androgenetic female-pattern alopecia in a subject in need of such treatment, comprising administering to the subject an androgenetic female-pattern alopecia inhibitory effective amount of melatonin.

2. The method of claim 1, wherein melatonin is administered at a dose of 0.1 to 10 mg per day.

3. The method of claim 1, wherein the administering is topical.

4. The method of claim 1, wherein the melatonin is in the form of a spray, a solution, a lotion, a cream, or an ointment.

5. The method of claim 1, comprising reducing a telegenic rate.

6. The method of claim 1, comprising enlarging hair diameter, increasing breaking force of hair, or a combination thereof.

7. The method of claim 6, wherein the hair is occipital hair.

* * * * *